(12) United States Patent
Kimura

(10) Patent No.: US 6,537,267 B1
(45) Date of Patent: Mar. 25, 2003

(54) METHOD FOR CHRONIC CATHETERIZATION OF THE COMMON BILE DUCT OF A LABORATORY RAT

(75) Inventor: Robert E. Kimura, Chicago, IL (US)

(73) Assignee: Rush-Presbyterian St. Luke's Medical Center, Chicago, IL (US)

( * ) Notice: Subject to any disclaimer, the term of this patent is extended or adjusted under 35 U.S.C. 154(b) by 0 days.

(21) Appl. No.: 09/918,869

(22) Filed: Jul. 31, 2001

(51) Int. Cl.$^7$ ........................ A61M 25/00; A01K 67/00
(52) U.S. Cl. ............................................. 604/523; 800/8
(58) Field of Search ............................... 800/8; 604/523

(56) References Cited

PUBLICATIONS

Beno et al., Endotoxin–induced reduction in biliary indocyanine green excretion rate in a chronically catheterized rat model, 2001, AM. J. Physiol. Gestrointest. Liver Physiol., vol. 280, pp. G858–G865.*

Lebrec et al., Hepatic vein catheterization in the rat, 1980, Pfluggers Arch., vol. 387, pp. 67–68.*

Kanz et al., Biliary function studies during multiple time periods in freely moving rats, a useful system and set of marker solutes, 1992, JPM, vol. 27, pp. 7–15.*

Beno, et al.; "Staphylococcal exterotoxin B potentiates LPS–induced hepatic dysfunction in chronically catheterized rats"; *Am J. Physiol Gastrointest Liver Physio*(280:G866–G872,2001).

Beno, et al.; "Endotoxin–induced reduction in biliary indocyanine green excretion rate in a chronically catheterized rat model"; *Am J. Physiol Gastrointest Liver Physiol*(280:G858–G865,2001).

Heitmeyer, et al.; "Improved Method for Bile Collection in Unrestrained Conscious Rats"; *Laboratory Animal Science*; vol. 42, No. 3, Jun. 1992.

Rolf, et al.; "Chronic Bile Duct Cannulation in Laboratory Rats"; *Laboratory Animal Science*; vol. 41, Jun. 1991.

Rath, et al.; "A new method of bile duct cannulation allowing bile collection and re–infusion in the conscious rat".

Wang, et al.; "A Comparison of Two Surgical Techniques for Preparation of Rats with Chronic Bile Duet Cannulae for the Investigation of Enterohepatic Circulation"; *Laboratory Animal Science*; vol. 44, No. 5, Jun. 1994.

Kan, et al.; "Biliary Function Studies During Multiple Time Periods in Freely Moving Rats A Useful System and Set of Marker Solutes"; *Journal of Pharmacological Methods 27*; 7–15 (1992) Elsevier Science Publishing Co., Inc.

Epstein, et al.; "A Model for Biliary and Vascular Access in the Unanesthetized, Unrestrained Rat"; *Physiology & Behavior*; vol. 48. pp–539–542; Pergamon Press 1990.

Balabaud, et al.; "Bile Collection in Free Moving Rats"; *Laboratory Animal Science*; © 1981 by the American Associaton for Laboratory Animal Science.

Enderlin,et al. "Technical Notes, Long Term Bile Collection in the Rat"; *Laboratory animal Science*; © 1977 by the American Associaton for Laboratory Animal Science; vol. 27.

Knapp,et al. "An Improved Technic for the Collection of Bile in the Unanesthetized Rat"; *Laboratory animal Science*; © 1971 by the American Association for Laboratory Animal Science; vol. 21, No. 3.

Xu, et al.; "Simultaneous Sampling of Blood, Bile, and Urine in Rats for Pharmacokinetic Studies"; *Journal of Pharmacological Methods*; 24, 203–208; © 1990; Elsevier Science Publishing Co., Inc.

* cited by examiner

*Primary Examiner*—Anne-Marie Falk
*Assistant Examiner*—Celine Qian
(74) *Attorney, Agent, or Firm*—Welsh & Katz, Ltd.

(57) ABSTRACT

The subject invention comprises a method for producing animals where the common bile duct is cannulated for use in the study of endotoxin-induced alterations in hepatic function by measuring changes in the maximal steady-state biliary excretion rate of the anionic dye, indocyanine green (ICG). In a further embodiment the hypatic vein is catheterized.

2 Claims, 3 Drawing Sheets

METHOD FOR CHRONIC CATHETERIZATION OF THE COMMON BILE DUCT OF A LABORATORY RAT

FIELD OF THE INVENTION

This invention relates to the modification of laboratory animals for use in clinical studies and more specifically, to chronic catheterization of bile ducts of rats.

Tumor necrosis factor-α (TNFα) is believed to be the primary mediator of endotoxin-induced hepatocellular dysfunction. This dysfunction results in decreased bile formation, a condition known as cholestasis. It has been shown that the endotoxin-induced TNFα response is dramatically attenuated by the surgical and nonsurgical stress associated with experimental protocols. In general, this condition, and others, can be evaluated in clinical studies by the use of chronically catheterized rats. Such rats have ligated common bile ducts, and a catheter connecting the bile duct to either a distal part of the bile duct or the intestine. In this use of such chronically catheterized rats, the bile duct will block or harbor bacterial colonies which adversely affect the study.

SUMMARY OF THE INVENTION

In the method of the subject invention, the common bile duct of a laboratory animal is cannulated but not ligated. The bile duct is left intact. Bile is siphoned by gravity from the catheter. In this manner, 100% of the bile is collected. The presence of the catheter does not alter hepatic function with respect to bile flow, bile acid flux, maximal indocyanine green biliary excretion, biliary gamma GT, or drug metabolism.

CONCISE DESCRIPTION OF THE DRAWINGS

The present invention will now be described in detail with respect to preferred embodiments thereof, which are to be taken together with the accompanying drawings, wherein.

DETAILED DESCRIPTION OF THE INVENTION

Figure 1:
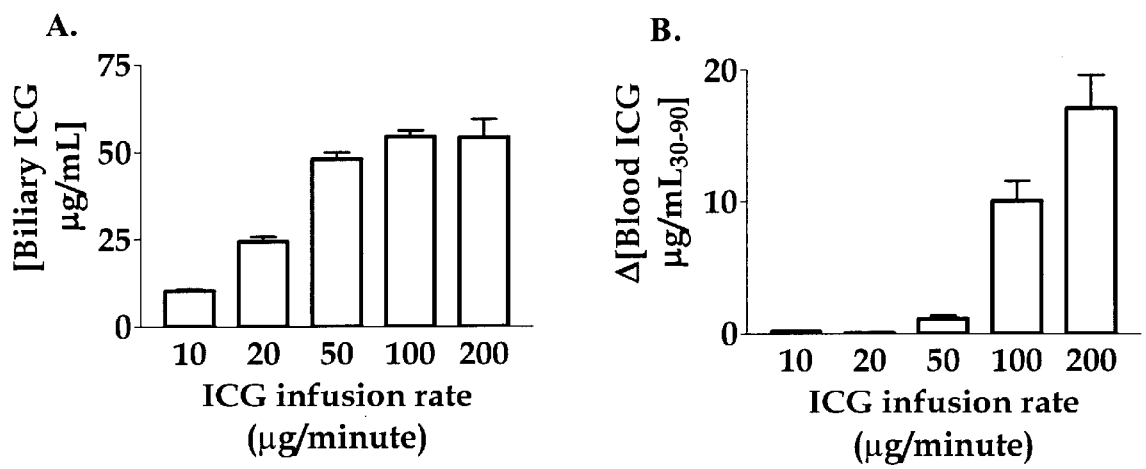
FIG. 1 is a graph showing the determination of maximal biliary ICG excretion rate.

In the subject invention, vascularly catheterized laboratory animal models such as dogs, cats, rats, monkeys and the like, were modified to include a chronic bile catheter. These models feature several advantages for studying endotoxin-induced hepatic dysfunction. First, rat models generate an unattenuated endotoxin-induced TNFα response because they are performed without the adverse effects of protocol-related stress. Second, normal hepatic and physiology and function is maintained because bile flow from the liver to the intestine is unimpeded and therefore, enterohepatic circulation of bile acids remains intact, permitting serial measurements of bile flow. Finally, the rat models minimize inter-animal variability because serial experiments can be performed on the same animal.

Reagents

Endotoxin (*E. coli* 0127:B8, Sigma Chemical, St Louis, Mo.) was prepared in sterile saline. Indocyanine green (ICG) was obtained from Akorn Industries (Decatur, Ill.). rTNFα (murine) was obtained from Genentech Inc. (San Francisco, Calif.).

Animals

A total of 72 adult male Sprague-Dawley rats (Charles River Laboratories, Wilmington, Mass.) weighing 325–350 g were used in this example. Rats were housed singly in standard cages and were fed chow and water ad libitum. The environment was temperature-and humidity-controlled, with lights on and off at 06:30 h and 16:30 h, respectively.

Operative Procedures

Operative procedures were performed as previously described. Briefly, the animals were anesthetized with 60 mg/kg ketamine and 5 mg/kg xylazine intramuscularly. Catheters were placed in the aorta, inferior vena cava (IVC) and duodenum under sterile conditions. A bile catheter was made by inserting the 0.5 cm tip of a 24-gauge Insyte catheter (Becton Dickinson Vascular Access, Sandy, Utah) into a 3 cm segment of silastic tubing. A 0.5 cm segment of PE60 tubing (Clay Adams, Parsippany, N.J.) was inserted into the other end of the silastic tubing, and the entire catheter was placed over a 24-gauge Insyte needle. After placement of the IVC and aortic catheters, the tip of the 24-gauge Insyte needle was introduced retrograde fashion into the common bile duct approximately 2 cm distal to the liver. Then, the bile catheter was advanced over the Insyte needle 0.25 cm into the bile duct, the Insyte needle was removed, and the catheter was secured with cyanoacrylate glue. The distal PE60 tubing was inserted into 3.5 inch intermittent infusion set tubing (no. 4871, Abbott Laboratories, North Chicago, Ill.) that had been passed from a cervical incision into the abdominal cavity. During this procedure the bile duct was not ligated and bile flow was not obstructed. The abdominal cavity was closed with 4-O silk suture. The infusion sets exiting the cervical incision were sutured securely to the back of the rat with 2-0 silk suture, and were glued postoperative with silicon to form a single unit. To maintain patency, all catheters were flushed daily.

Measurement of Maximum Biliary ICG Excretion

Bile was obtained through the bile catheter by inserting a 23-gauge infusion set needle (Abbott Laboratories) from which all but 0.5 in of tubing had been removed, and approximately 24 inches of saline-filled PE 60 tubing attached. A sterile 1.5 mL sampling tube was attached to the tubing end, and bile was withdrawn by suspending the sampling tube below the cage using negative pressure. Bile was collected into tared sampling tubes at 5 minute intervals during a 90 minute period during which ICG was infused into the IVC at 50 μg/minute. ICG, 1 mL/h was delivered by a Razel Scientific (Stamford, Conn.) infusion pump with a 3 mL Becton Dickinson (Franklin Lakes, N.J.) syringe.

Bile flow rate was calculated using the net sampling tube weight assuming a bile density of 1 g/mL. A total of 10 μL of bile from each sample tube was aliquoted to determine ICG concentration. The remainder of the bile was infused into the duodenal catheter to maintain enterohepatic circulation of bile acids. Biliary ICG concentrations were measured spectrophotometrically at wavelength 805 nm. Biliary ICG excretion was calculated for each 5 minute interval by multiplying the bile flow rate by the biliary ICG concentration.

Experimental Design

Experiments were performed at least 4 days postoperatively because the effects of surgical stress on the endotoxin-induced cytokine response should be no longer present at this time. At this time the animals had achieved at least 95% of their preoperative weight.

EXAMPLE I
Effect of Endotoxin on Hepatic Function

Rats were assigned to receive one of three doses of endotoxin infused into the IVC over 30 seconds: 0 μg/kg (Control, n=7), 100 μg/kg (n=9), or 1000 μg/kg (n=8). The animals were anesthetized with ketamine (60 mg/kg) and xylazine (5 mg/kg) intramuscularly. Catheters were placed in the aorta, inferior vena cava (IVC), portal vein (PV) and duodenum as previously described. Rates of biliary ICG excretion and bile flow were measured at baseline (time 0) and then 6 h and 24 h post-endotoxin administration. Aortic blood samples (0.2 ml) were collected at 0 and 90 minute for determination of corticosterone and TNFα concentrations, respectively. Following each blood draw, the animals were transfused with an equal volume of blood obtained immediately prior to transfusion from other untreated chronically catheterized rats that were previously designated as donors. Samples were aliquoted and stored at −80° C. until analyzed. TNFα was measured by ELISA (Genzyme, Cambridge, Mass.). Corticosterone was measured by RIA (ICN Biomedicals Inc., Costa Mesa, Calif.). For a subgroup of 8 rats, these biliary measures were performed at 4 additional time points: 2, 4, 48 and 72 h post-endotoxin infusion (0 μg/kg, Control, n=2), 100 μg/kg (n=3), or 1000 μg/kg (n=3).

Figure 5:
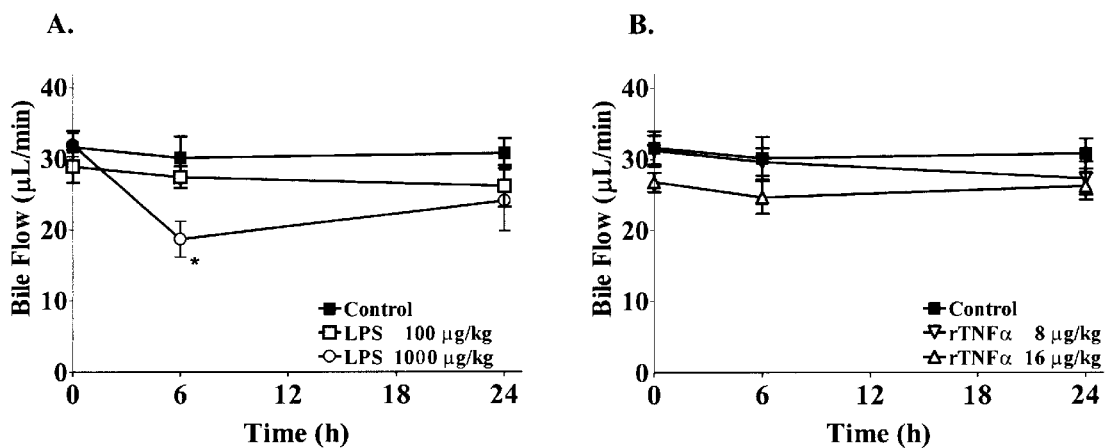
FIGS. 5a and 5b are graphs showing the effect of endotoxin and rTNFα on bile flow rate.

For rats who received only LPS, mean bile flow rates at 6 and 24 h were unchanged from baseline values following infusion of 100 μg/kg endotoxin (FIG. 5a). However, infusion of 1000 μg/kg endotoxin resulted in a reduction in mean bile flow rate of 42% ($p<0.001$) at 6 h and 25% (NS) at 24 h when compared to baseline values. Peak serum TNFα concentrations were 90.9±16.2 ng/mL and 129.6±24.4 ng/mL following infusion of 100 μg/kg and 1000 μg/kg endotoxin, respectively. No differences in mean bile flow rate at 6 and 24 h were noted in the control group when compared to baseline values (FIG. 5A). The mean baseline corticosterone concentration for all rats reported throughout this study was 46.4±14.8 ng/mL (range 34 to 110 ng/mL).

Mean serum TNFα concentrations 1 minute following rTNFα administration were 122.8±15.6 ng/mL and 252.6±28.5 ng/mL for the 8 μg/kg and 16 μg/kg doses, respectively. Although greatly decreased mean serum TNFα concentrations were significantly elevated for up to 90 or 120 minutes following rTNFα administration of 8 μg/kg and 16 μg/kg, respectively (data not shown). No TNFα was detected in the serum after 120 minutes. Mean bile flow rates at 6 and 24 h were unchanged from baseline values following rTNFα administration (FIG. 5b).

EXAMPLE II
Effect of rTNFα on Hepatic Function

In a separate group of animals, the postulation that TNFα is the primary mediator of the endotoxin-induced inhibition of bile flow rate was investigated. The animals were anesthetized with ketamine (60 mg/kg) and xylazine (5 mg/kg) intramuscularly. Catheters were placed in the aorta, inferior vena cava (IVC), portal vein (PV) and duodenum as previously described. For these experiments, rates of biliary ICG excretion and bile flow following bolus infusion of 8 μg/kg (n=5) or 16 μg/kg (n=4) of rTNFα was measured. These rTNFα doses were chosen to simulate (125 ng/mL) or double (250 ng/mL) peak serum TNFα concentrations observed in this study following infusion of 1000 μg/kg endotoxin. TNFα was not detectable in the serum after 120 minutes (½ life of 15.6 minutes, $r^2=0.96$) following infusion of 8 μg/kg rTNFα. Rates of biliary ICG excretion and bile flow were measured immediately prior to rTNFα administration (baseline) and again at 4.5 and 22.5 h post-rTNFα administration. Because endotoxin-induced peak TNFα was observed at 1.5 h post-endotoxin infusion, we measured hepatic function at 4.5 h and at 22.5 post-rTNFα administration. These measures simulated the timing of endotoxin-induced TNFα effects on hepatic functions at 6 and 24 h. Aortic blood samples (0.2 mL) were obtained immediately prior to and 1 minute after rTNFα administration for determination of corticosterone and TNFα concentrations, respectively. Following each blood draw, the animals were transfused with an equal volume of blood obtained immediately prior to transfusion from other untreated chronically catheterized rats that were previously designated as donors.

Figure 6:
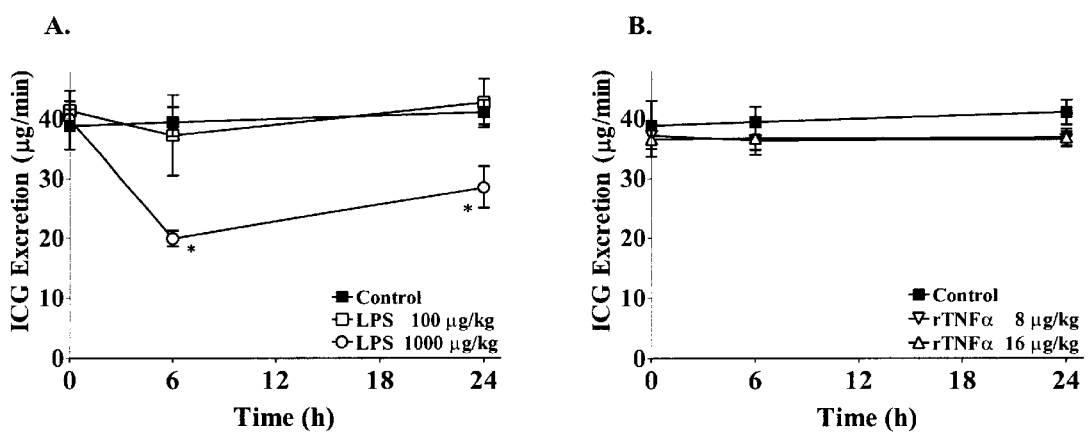
FIGS. 6a and 6b are graphs showing the effect of endotoxin and rTNFα on biliary ICG clearance rate.

Infusion of 1000 μg/kg endotoxin resulted in a reduction in mean biliary ICG clearance of 50 % ($p<0.001$) at 6 h and 29% ($p<0.01$) at 24 h when compared to baseline values (FIG. 6a). Mean biliary ICG clearance rates at 6 and 24 h were unchanged from baseline values following infusion of 100 μg/kg (FIG. 6a). No differences in biliary ICG clearance rate at 6 and 24 h were noted in the control group compared to baseline values (FIG. 6a). Mean biliary ICG clearance rates at 6 and 24 h were unchanged from baseline values following rTNFα administration of 8 μg/kg and 16 μg/kg (FIG. 6b).

EXAMPLE III
Determination of Maximal Biliary ICG Excretion Rate

To establish a sensitive and reliable measure of hepatic dysfunction, the maximal biliary ICG excretion rate under physiologic conditions was determined. This measure, which detected even minor changes in biliary ICG excretion, was critical to subsequent primary studies. The animals were anesthetized with ketamine (60 mg/kg) and xylazine (5 mg/kg) intramuscularly. Catheters were placed in the aorta, inferior vena cava (IVC), portal vein (PV) and duodenum as previously described. The blood concentrations and biliary excretion rates of ICG was measured during a constant infusion of ICG at 10, 20, 50, 100, and 200 μg/minute for 90 minutes in 8 rats that served as their own controls for the different doses on separate days. No residual ICG from the previous day's infusion was observed in the bile for any animal at any time. Biliary ICG excretion was measured as described above. Aortic blood samples (0.25 mL) were collected every 10 minutes and analyzed for ICG concentration. Following each blood draw, the animals were transfused with an equal volume of blood obtained immediately prior to transfusion from other untreated chronically catheterized rats that were previously designated as donors. The data revealed that maximum biliary ICG excretion rate occurred following ICG infusion rates of 50 μg/minute or greater (FIG. 1a). After an initial 30 minute equilibration period mean biliary ICG excretion remained at a steady state concentration between 30 and 90 minutes of ICG infusion. Although higher concentrations of ICG infusion (100 and 200 μg/minute) did not yield a greater biliary ICG excretion rate between 30 and 90 minutes (FIG. 1a), they did significantly increase mean blood ICG concentrations during the time period of steady state mean biliary ICG excretion between 30 and 90 minutes of ICG infusion compared to infusion of ICG at 50 μg/minute ($\Delta[ICG_{90-30}]$, FIG. 1b). The bile flow rate was unaffected by any of the tested ICG concentrations. The data from this preliminary study indicated that the maximal rate of ICG uptake and excretion from the liver into the bile occurred following ICG infusion of 50 μg/minute, so this infusion rate was incorporated into the methodology for our primary study.

EXAMPLE IV
Accuracy of Bile Flow Rate Calculation

This example confirms that during bile sampling, all bile in the common bile duct was collected, and that no bile bypassed the bile catheter, being secreted into the intestine. Since ICG is excreted exclusively into the bile, the accuracy of the calculation for bile flow rate was determined by comparing the amount of ICG infused into the IVC with that excreted into the bile. The animals were anesthetized with ketamine (60 mg/kg) and xylazine (5 mg/kg) intramuscularly. Catheters were placed in the aorta, inferior vena cava (IVC), portal vein (PV) and duodenum as previously described.

Figure 2:
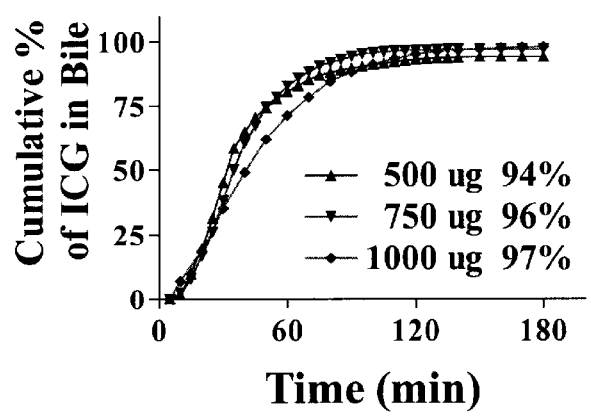
FIG. 2 is a graph showing the accuracy of bile flow rate calculation.

8 rats that served as their own controls for infusions of three doses of ICG (500, 750 and 1000 μg) were studied on three separate days. No residual ICG from the previous day's infusion was observed in the bile of any animal for any study day. For all ICG doses, a 1 mL bolus was infused, and ICG concentration in the bile was measured at 10 minute intervals for 2.5 h postinfusion. Following a 180 minute period a mean of 95.6±4.7% of the ICG infused was recovered from bile for all ICG doses (FIG. 2), demonstrating that the subject method accurately calculates bile flow.

EXAMPLE V

Effect of chronic biliary catheterization on hepatic pathology and bile flow. The animals were anesthetized with ketamine (60 mg/kg) and xylazine (5 mg/kg) intramuscularly. Catheters were placed in the aorta, inferior vena cava (IVC), portal vein (PV) and duodenum as previously described.

In 10 rats, serial liver function measurements and histologic examination of the liver and bile ducts were performed at scheduled time points over a 28-day period following bile duct catheterization. No hepatic or biliary histologic abnormalities were noted and mean values for liver function enzymes including ALT, alkaline phosphatase, γGT and albumin were unchanged during this time (data not shown).

Figure 3:
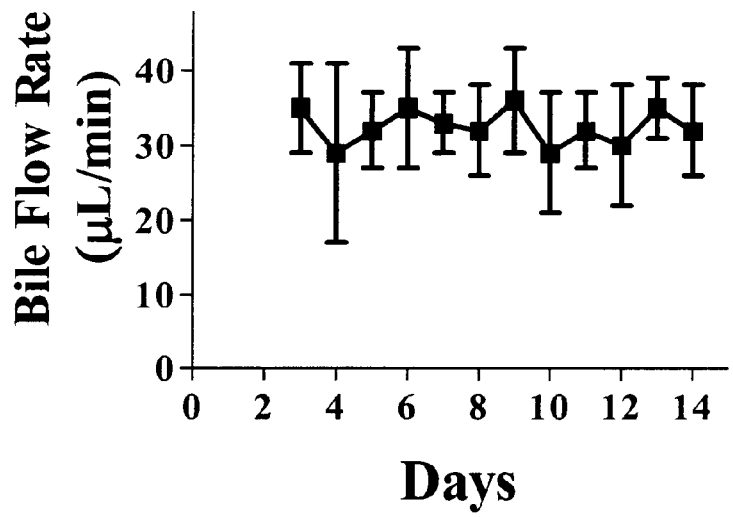
FIG. 3 is a graph showing effect of chronic biliary catheterization on bile flow rates.

To assure that measures of bile flow remained constant over the time that experiments were performed, the bile flow rate was measured daily for 10 rats from 3 to 14 days postsurgery. For this set of experiments, bile flow rate was measured at 5 minute intervals for a total of 30 minutes. The data revealed that mean bile flow rates were constant over this time period (FIG. 3). Of the original 10 rats in this set of experiments, the bile flow rate of 3 rats was measured for an additional 10 days. Mean bile flow rate for these rats was constant for 24 days postsurgery (data not included in FIG. 3).

EXAMPLE VI
Effect of Endogenous Bile Replacement on Bile Flow

Figure 4:
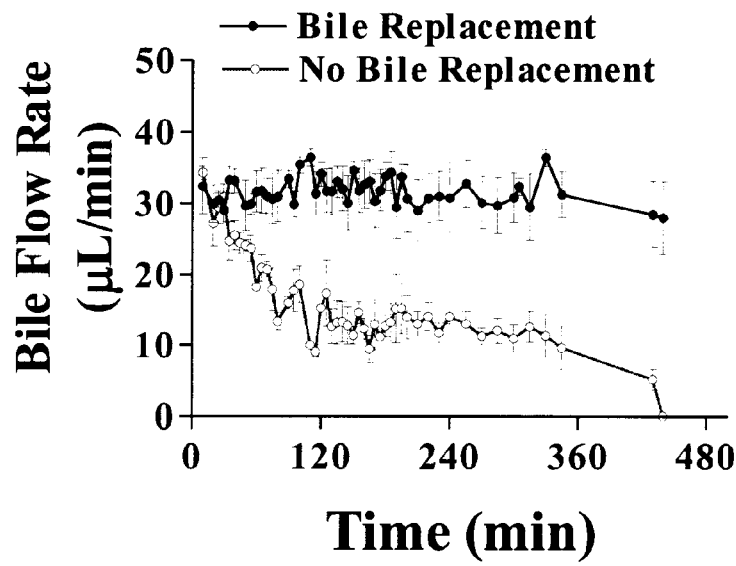
FIG. 4 is a graph showing the effect of endogenous bile replacement on bile flow.

In this example, the hypothesis that reduced bile flow rates resulted from continuous bile sampling that depleted bile acid was tested. The animals were anesthetized with ketamine (60 mg/kg) and xylazine (5 mg/kg) intramuscularly. Catheters were placed in the aorta, inferior vena cava (IVC), portal vein (PV) and duodenum as previously described. Because the model permits replacement of collected bile and maintains enterohepatic bile circulation, mean bile flow rate was compared with and without the replacement of bile through a duodenal catheter (FIG. 4). Chronically catheterized rats were assigned randomly to control (without bile replacement, n=5); or experimental (with bile replacement, n=5) groups. For both groups of rats, bile flow rate was measured at 5 minute intervals for 4 h and at 15 to 60 minute intervals for an additional 4 h between 4 and 7 days postsurgery. Data revealed a significantly lower mean bile flow rate for the control group (FIG. 4), beginning at 35 minutes after bile sampling had begun (p<0.05). In contrast, bile flow rate remained constant for experimental animals, suggesting that replacement of bile into the duodenum permits serial bile collection (up to 4 h) without significantly altering bile flow rate. The data demonstrate a dose- and time-dependent decrease in the rates of bile flow and biliary excretion of ICG following endotoxin infusion, and suggest that TNFα is not the singular mediator of this response. Whereas the endotoxin dose of 1000 μg/kg resulted in significant reduction from baseline values for rates of biliary ICG excretion at 6 and 24 h and of bile flow at 6 h postinfusion, no changes from baseline values were noted for 100 μg/kg of endotoxin or for the controls. The 1000 μg/kg and 100 μg/kg doses of endotoxin resulted in peak serum TNFα concentrations of 129.6±24.2 and 90.9±16.2 ng/mL, respectively.

Thus, 100 μg/kg of endotoxin caused a significant and sustained increase in TNFα without affecting the rates of biliary ICG excretion or bile flow. Isolation of the effects of TNFα was attempted by infusing two doses of rTNFα that achieved either the same peak serum concentration of TNFα or twice the peak serum concentration. These examples, designed to examine the singular role of TNFα in mediating endotoxin-induced hepatic dysfunction, revealed no change from baseline rates for biliary ICG excretion or bile flow following rTNFα administration at either 8 or 16 μg/kg in the absence of endotoxin infusion. This finding strongly suggests that TNFα is not the singular mediator of endotoxin-induced hepatic dysfunction because these rTNFα doses yielded higher mean serum TNFα concentrations than those achieved with 1000 μg/kg of endotoxin infusion (Table I).

TABLE I

Summary of peak serum TNFα and 6 h rates of biliary ICG clearance and bile flow.

| Treatment | Peak TNFa | % decrease 6 h. Biliary ICG clearance. | % decrease 6 h. Bile flow rate. |
|---|---|---|---|
| 10 μg/kg endotoxin (data not graphed) | 48.6 ± 13.3 | 0 | 0 |
| 100 μg/kg endotoxin | 90.9 ± 16.2 | 1 | 0 |
| 1000 μg/kg endotoxin | 129.6 ± 24.4 | 50* | 42* |
| 16 μg/kg rTNFα | 252.6 ± 28.5 | 0 | 0 |
| 8 μg/kg rTNFα | 122.8 ± 15.6 | 0 | 0 |

Data are mean ± SEM.
*p < 0.01 by repeated measures ANOVA.

EXAMPLE VII

The animals were anesthetized with ketamine (60 mg/kg) and xylazine (5 mg/kg) intramuscularly. Catheters were placed in the aorta, inferior vena cava (IVC), portal vein (PV) and duodenum as previously described.

The hepatic venous catheter was made in similar fashion to the portal venous catheter by inserting 0.5 cm segment of PE-60 tubing (Clay Adams, Parsippany, N.J.) into both ends of a 6 cm segment of silastic tubing (ID=0.03i; Baxter, McGaw Park, Ill.) placed over a 25-gauge spinal needle. Caudally retracting the left lobe of the liver exposed the hepatic vein. Approximately 5 mm distal from the hepatic vein the catheter was inserted into the liver and then tunneled through the liver into the hepatic vein. The catheter was glued in place with cyanoacrolate glue. The distal end was attached to the tubing from a 3.5i intermittent infusion set (no. 4871, Abbott Laboratories, North Chicago, Ill.) previously tunneled from a cervical incision into the abdominal cavity. The abdominal cavity was closed with 4-O silk suture. The infusion sets exiting the cervical incision were sutured to the back of the rat using 2-O silk suture and secured with silicon to form a single unit. Catheters were flushed daily to maintain patency.

Sampling was verified by infusing into the inferior vena cava high concentrations of 14 C[PEG 4000], an inert substance that remains in the vascular space. Portal venous and hepatic venous blood was sampled simultaneously. The concentration of 14 C[PEG 4000] was similar in portal venous and hepatic venous blood, indicating no significant contamination of inferior vena cava blood in the hepatic venous blood sample.

The above findings are inconsistent with other studies, conducted with both humans and rats, in which $TNF\alpha$ has been implicated as the major mediator of cholestasis during endotoxemia. In a series of human studies, investigators demonstrated that immunotherapy with $rTNF\alpha$ induces cholestasis in humans. Using a rat model, it has been demonstrated that administration of anti-$TNF\alpha$ antibody prior to endotoxin infusion provided protection from endotoxin-induced bile acid accumulation. In separate research with rats, the administration of extremely high concentrations of parenteral $rTNF\alpha$ (0.2–3.6 mg/kg) induced severe sepsis-like responses including altered cardiac output, severe hepatic dysfunction and death. In order to minimize these toxic effects, a lower exogenous $rTNF\alpha$ (0.05 and 0.25 mg/kg) was administered to rats over 30 minutes. Although these lower $rTNF\alpha$ doses did not alter the hepatic microcirculation, ICG clearance was reduced following the 0.25 mg/kg dose, but was unaffected with the 0.05 mg/kg dose. These lines of evidence lead one to conclude that elevated $TNF\alpha$ concentrations play a pivotal role in hepatocellular dysfunction.

In contrast, the results of the above examples do not support the conclusion that $TNF\alpha$ is the singular mediator of reduced ICG excretion. A major difference between the above methodologies and others is that others infused very high $rTNF\alpha$ doses for 30 minutes to achieve measurable differences in hepatic ICG clearance, whereas, we administered a single bolus infusion of $rTNF\alpha$. However, the bolus infusion of $rTNF\alpha$ did result in significantly elevated concentrations of $TNF\alpha$ for up to 120 minutes, approximating the length of significantly elevated concentrations of $TNF\alpha$ following endotoxin challenge. To further control for the possibility that a bolus infusion may not accurately reflect the more sustained endotoxin-induced $TNF\alpha$ response, we infused endotoxin doses of 100 $\mu$g/kg to achieve and sustain comparably elevated $TNF\alpha$ concentrations to those in response to 1000 $\mu$g/kg, and still found no alteration from mean baseline rates of biliary ICG excretion or bile flow. Most importantly, the extremely elevated $rTNF\alpha$ concentrations that reduced ICG clearance in others' studies cannot be achieved in acute endotoxemic models, precluding generalizability of their findings to physiologic models of endotoxin-induced hepatic dysfunction.

The method of the subject invention has several advantages for studying endotoxin-induced alterations in biliary ICG clearance. Previous studies revealed that surgical stress dramatically attenuates the endotoxin-induced $TNF\alpha$ response. it is speculated that the lack of protocol-related stress in the model herein permits earlier detection of kinetic differences in the intracellular regulation and functional kinetics of ICG. These speculations are consistent with previous work that suggests surgical stress elevates glucocorticoids, which in turn attenuates endotoxin-induced hepatic dysfunction. For example, analysis of the rat mrp2 gene promoter revealed multiple glucocorticoid response elements, which may protect hepatic function during stress. In studies with rats, exogenous dexamethasone inhibited the endotoxin-induced translocation of mrp2, the reduction of mRNA, and the excretion of anionic dye, while the bile flow rate remains unaffected.

The chronically catheterized rat model of the subject invention controls for these effects, as evidenced by the finding that the control animals demonstrated constant biliary ICG excretion and bile flow rate over extended periods. In contrast to other methodologies, the model of the subject invention did not interrupt normal enterohepatic circulation of bile, because collected bile was reinfused into a duodenal catheter that was inserted 2 cm distal to the sphincter of Oddi, which is proximal to the terminal ileum, the site of bile acid reabsorption. This procedural adaptation maintained baseline bile flow rates in the experimental animals for up to eight hours of serial bile collection without the use of exogenous bile acids.

Another advantage of the method of the subject invention is the ability to detect even minor alterations in hepatic function. Preliminary studies revealed that the system of the subject invention induces maximum ICG transport without significant accumulation of ICG in the blood, as evidenced by the maintenance of steady state ICG secretion into bile. Preliminary data revealed that the continuous infusion of ICG at 50 $\mu$g/min produced the maximum ICG excretion rate. ICG was infused at a constant rate because this method maintains steady state biliary ICG excretion over the entire 90 minute period used in this study. In contrast, bolus or sequential bolus infusions do not maintain a steady state biliary excretion of ICG. Indeed, in our studies, 30 minutes of ICG infusion is required to obtain steady state biliary ICG excretion. Therefore, we collected our data was collected from each animal at 12 individual time points during steady state biliary ICG excretion.

What is claimed is:

1. A method for modifying laboratory animals for use in clinical studies comprising placing a catheter over a needle, introducing the needle into the hepatic vein, advancing the catheter over the needle into the hepatic vein of a laboratory animal, removing the needle and securing the catheter to the hepatic vein with adhesive.

2. A method for modifying laboratory animals for use in clinical studies comprising placing a catheter over a needle, introducing the needle into the common bile duct, advancing the catheter over the needle into the bile duct of a laboratory animal removing the needle and securing the catheter to the bile duct with adhesive.

* * * * *